United States Patent
Hamada (10) Patent No.: US 9,282,324 B2
(45) Date of Patent: Mar. 8, 2016

(54) MEDICAL IMAGE DIAGNOSIS APPARATUS AND IMAGE PROCESSING APPARATUS

(71) Applicants: Kabushiki Kaisha Toshiba, Minato-ku (JP); Toshiba Medical Systems Corporation, Otawara-shi (JP)

(72) Inventor: Kenji Hamada, Otawara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/067,367

(22) Filed: Oct. 30, 2013

(65) Prior Publication Data

US 2014/0055452 A1 Feb. 27, 2014

Related U.S. Application Data

(63) Continuation of application No. PCT/JP2012/062216, filed on May 11, 2012.

(30) Foreign Application Priority Data

May 19, 2011 (JP) .................. 2011-112299

(51) Int. Cl.
*H04N 13/04* (2006.01)
*A61B 8/00* (2006.01)
(Continued)

(52) U.S. Cl.
CPC .............. *H04N 13/0447* (2013.01); *A61B 8/14* (2013.01); *A61B 8/466* (2013.01); *A61B 8/483* (2013.01);
(Continued)

(58) Field of Classification Search
CPC combination set(s) only.
See application file for complete search history.

(56) References Cited

U.S. PATENT DOCUMENTS 8,004,560 B2  8/2011  Sato et al.
8,351,758 B2  1/2013  Yamaji et al.
(Continued)

FOREIGN PATENT DOCUMENTS

CN  101842734 A  9/2010
JP  2000-078611 A  3/2000
(Continued)

OTHER PUBLICATIONS

International Search Report mailed Jun. 12, 2012 for PCT/JP2012/062216 filed on May 11, 2012 with English translation.
(Continued)

*Primary Examiner* — Maurice L McDowell, Jr.
(74) *Attorney, Agent, or Firm* — Oblon, McClelland, Maier & Neustadt, L.L.P.

(57) ABSTRACT

A medical image diagnosis apparatus according to an embodiment includes a rendering processing unit, a display unit, and a control unit. The rendering processing unit is configured to perform rendering processing from a plurality of viewpoints on volume data that is three-dimensional medical image data to create a parallax image group composed of a predefined number of parallax images. The display unit is configured to display the parallax image group to display a stereoscopic image recognized stereoscopically by an observer. The control unit configured to perform control so that a composite image group of the parallax image group and an information image is displayed on the display unit in such a manner that a first region displaying the parallax image group on the display unit is distinguishable from a second region displaying the information image indicating information other than the parallax image group on the display unit.

14 Claims, 8 Drawing Sheets

(51) Int. Cl.
*A61B 8/08* (2006.01)
*H04N 13/02* (2006.01)
*A61B 8/14* (2006.01)
*G06T 19/00* (2011.01)

(52) U.S. Cl.
CPC ............... *A61B 8/486* (2013.01); *A61B 8/488* (2013.01); *A61B 8/5246* (2013.01); *G06T 19/00* (2013.01); *H04N 13/0275* (2013.01); *H04N 13/0282* (2013.01); *G06T 2210/41* (2013.01)

(56) References Cited

U.S. PATENT DOCUMENTS

| | | |
|---|---|---|
| 2002/0008906 A1 | 1/2002 | Tomita |
| 2010/0128116 A1 | 5/2010 | Sato et al. |
| 2011/0228997 A1* | 9/2011 | Sharp et al. ............... 382/131 |
| 2011/0235066 A1* | 9/2011 | Sakuragi ....................... 358/1.6 |
| 2012/0038632 A1* | 2/2012 | Matsunaga et al. ........... 345/419 |
| 2013/0188028 A1 | 7/2013 | Yamaji et al. |

FOREIGN PATENT DOCUMENTS

| | | |
|---|---|---|
| JP | 2001-326947 A | 11/2001 |
| JP | 2003-339703 | 12/2003 |
| JP | 2004-354540 A | 12/2004 |
| WO | 2009/057409 A1 | 5/2009 |
| WO | 2010/095403 A1 | 8/2010 |

OTHER PUBLICATIONS

International Written Opinion mailed Jun. 12, 2012 for PCT/JP2012/062216 filed on May 11, 2012.

Chinese Office Action issued Sep. 24, 2014, in Patent Application No. 201280000691.4.

* cited by examiner

MEDICAL IMAGE DIAGNOSIS APPARATUS AND IMAGE PROCESSING APPARATUS

CROSS-REFERENCE TO RELATED APPLICATIONS

This application is a continuation of International Application No. PCT/JP2012/062216, filed on May 11, 2012 which claims the benefit of priority of the prior Japanese Patent Application No. 2011-112299, filed on May 19, 2011, the entire contents of which are incorporated herein by reference.

FIELD

Embodiments described herein relate generally to a medical image diagnosis apparatus and an image processing apparatus.

BACKGROUND

Recently, a display apparatus for displaying a stereoscopic image that human beings can recognize as a three-dimensional space by adopting a projection method using binocular parallax has been put into practical use. An example of such a display apparatus is a monitor for displaying a stereoscopic image that an observer can view stereoscopically with naked eyes using parallax images (e.g. nine parallax images) taken from a plurality of viewpoints using a light beam controller such as a lenticular lens, for example.

Medical image diagnosis apparatuses, such as an ultrasound diagnosis apparatus, an X-ray computed tomography (CT) apparatus, and a magnetic resonance imaging (MRI) apparatus, that can create three-dimensional medical image data (volume data) have been put into practical use. In the related art, the volume data created by the medical image diagnosis apparatuses becomes a two-dimensional image (a rendering image) through various kinds of image processing (rendering processing) and is displayed in two-dimensions on a general-purpose monitor.

For example, volume data created by a medical image diagnosis apparatus becomes a two-dimensional image (a volume rendering image) reflecting three-dimensional information through volume rendering, and is displayed in two-dimensions on a general-purpose monitor. However, the volume rendering image displayed on a two-dimensional display surface on the general-purpose monitor provides a feeling of shallow depth, whereby an observer can hardly determine whether an interested region is actually placed in the front side or the rear side.

Therefore, it is examined that the volume rendering image created by performing volume rendering from a plurality of viewpoints on the volume data created by the medical image diagnosis apparatus is displayed stereoscopically on a monitor capable of providing stereoscopic viewing. Because medical images require an image quality with contrast, "black" is generally used for a background color on medical images. In addition, for a background color of characters or other information displayed together with medical images, black is generally used. As a result, the feeling of the depth of medical images to be viewed stereoscopically may be reduced.

DETAILED DESCRIPTION

A medical image diagnosis apparatus according to an embodiment includes a rendering processing unit, a display unit, and a control unit. The rendering processing unit is configured to perform rendering processing from a plurality of viewpoints on volume data that is three-dimensional medical image data to create a parallax image group composed of a predefined number of parallax images. The display unit is configured to display the parallax image group created by the rendering processing unit to display a stereoscopic image recognized stereoscopically by an observer. The control unit configured to perform control so that a composite image group of the parallax image group and an information image is displayed on the display unit in such a manner that a first region displaying the parallax image group on the display unit is distinguishable from a second region displaying the information image indicating information other than the parallax image group on the display unit.

Exemplary embodiments of a medical image diagnosis apparatus and an image processing apparatus are described below in greater detail with reference to the accompanying drawings. Hereinafter, an ultrasound diagnosis apparatus will be described as an example of the medical image diagnosis apparatus. Some terms used in the embodiments below are defined as follows. A "parallax image group" is an image group created by performing volume rendering processing on volume data with the viewpoint position being moved by a predetermined parallax angle. That is to say, "the parallax image group" is composed of a plurality of "parallax images" having different "viewpoint positions". A "parallax angle" is an angle determined between viewpoint positions adjacent to each other out of viewpoint positions set for creating "the parallax image group" and a predetermined position in a space represented by volume data (e.g. the center of the space). A "number of parallax" is the number of "parallax images" required for an image to be viewed stereoscopically on a stereoscopic display monitor. A "nine-parallax image" described hereinafter is a "parallax image group" composed of nine "parallax images". A "two-parallax image" described hereinafter is a "parallax image group" composed of two "parallax images".

Figure 1:
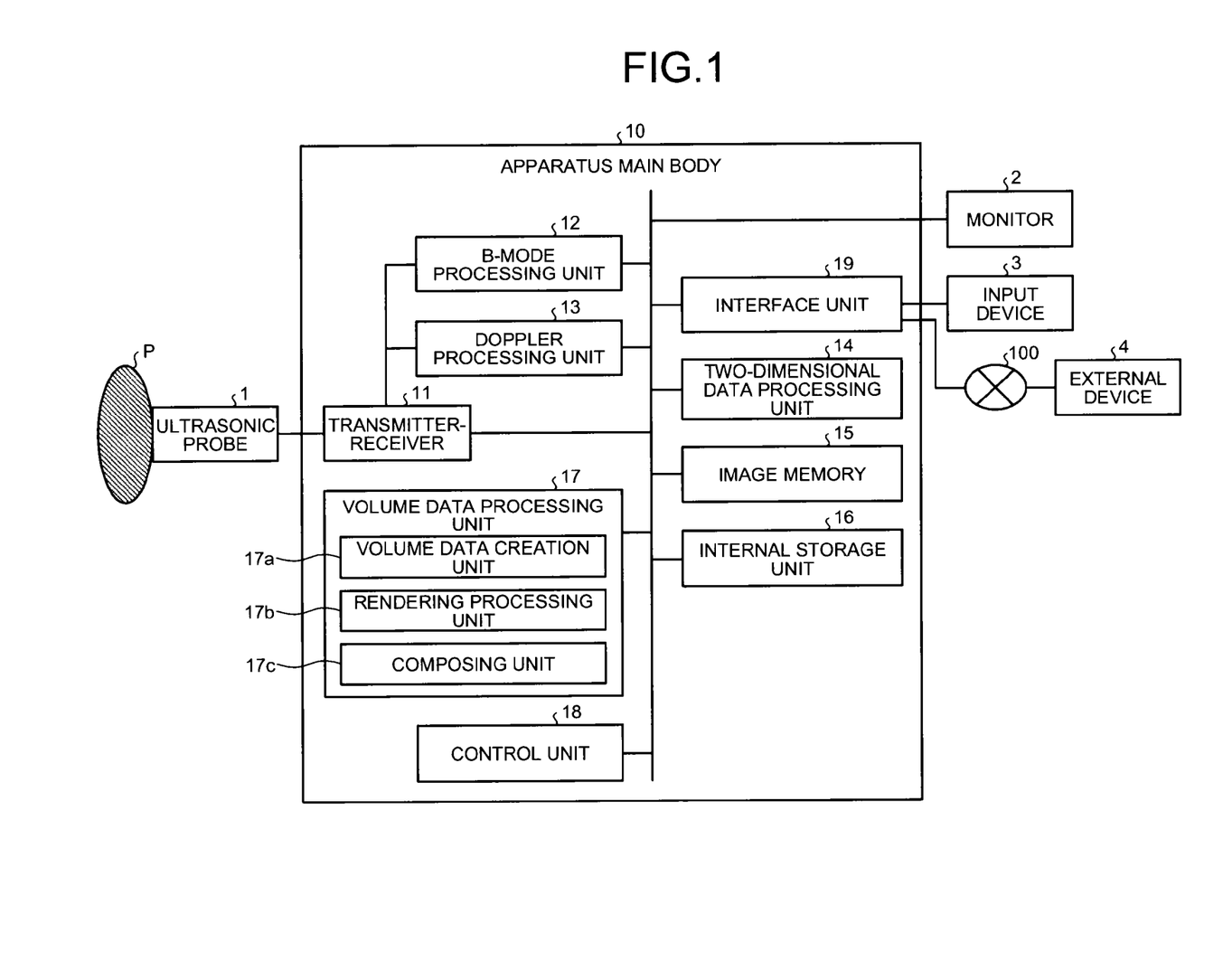
FIG. 1 is a diagram for explaining an example of a structure of an ultrasound diagnosis apparatus according to a first embodiment.

Firstly, a structure of an ultrasound diagnosis apparatus according to a first embodiment will be described. FIG. 1 is a diagram for explaining an example of a structure of an ultrasound diagnosis apparatus according to a first embodiment. As illustrated in FIG. 1, the ultrasound diagnosis apparatus according to the first embodiment includes an ultrasonic probe 1, a monitor 2, an input device 3, and an apparatus main body 10. The apparatus main body 10 is coupled to an external device 4 through a network 100.

The ultrasonic probe 1 includes a plurality of piezoelectric transducer elements that generate ultrasonic waves based on driving signals provided by a transmitter-receiver 11 included in the apparatus main body 10, which will be described later. The ultrasonic probe 1 receives reflected waves from a subject P and converts them to electrical signals. The ultrasonic probe 1 includes a matching layer provided on the piezoelectric transducer elements and a backing material preventing transmission of ultrasonic waves from the piezoelectric transducer element backwards. The ultrasonic probe 1 is detachably coupled to the apparatus main body 10.

When the ultrasonic probe 1 transmits ultrasonic waves to the subject P, the transmitted ultrasonic waves are reflected one after another on a discontinuity surface of acoustic impedance in a tissue of the subject P, and received by the plurality of piezoelectric transducer elements included in the ultrasonic probe 1 as reflected wave signals. Amplitude of the reflected wave signals received depends on a difference of impedance on the discontinuity surface where the ultrasonic waves are reflected. The reflected wave signals when the transmitted ultrasonic pulses are reflected on a surface of a moving object such as bloodstream and cardiac walls receive frequency shift due to the Doppler effect. The extent of the shift depends on an amount of velocity component of the moving object with respect to a transmission direction of the ultrasonic waves.

Here, the ultrasonic probe 1 according to the first embodiment is an ultrasonic probe that scans the subject P in two dimensions using ultrasonic waves and can also scan the subject P in three dimensions. Specifically, the ultrasonic probe 1 according to the first embodiment may be a mechanical scanning probe that scans the subject P in three dimensions, by swinging a plurality of ultrasonic transducer elements that scan the subject P in two dimensions by a predetermined angle (a swing angle). The ultrasonic probe 1 according to the first embodiment may also be a two-dimensional ultrasonic probe where a plurality of ultrasonic transducer elements are arranged in a matrix, thereby being able to scan the subject P in three dimensions using ultrasonic waves. The two-dimensional ultrasonic probe can also scan the subject P in two dimensions by converging and transmitting the ultrasonic waves.

The input device 3 is coupled to the apparatus main body 10 through an interface unit 19 described later. The input device 3 has a mouse, a keyboard, a button, a panel switch, a touch command screen, a foot switch, a trackball, or the like to receive various kinds of setting demands from an operator of the ultrasound diagnosis apparatus, then transfer the various kinds of setting demands thus received to the apparatus main body 10.

The monitor 2 displays a graphical user interface (GUI) for enabling the operator of the ultrasound diagnosis apparatus to input the various kinds of setting demands using the input device 3, or displays, for example, an ultrasonic image created in the apparatus main body 10.

The monitor 2 according to the first embodiment is a monitor that can be viewed stereoscopically (hereinafter, referred to as a stereoscopic display monitor). The stereoscopic display monitor will be described below.

A general-purpose monitor that is currently the most predominant displays two-dimensional images in two dimensions, not stereoscopically. If an observer desires to view two-dimensional images stereoscopically on such a general-purpose monitor, an apparatus that outputs images to such a general-purpose monitor may need to cause the monitor to display two-parallax images that the observer can view stereoscopically in parallel using a parallel method or a crossover method, or an apparatus that outputs images to such a general-purpose monitor may need to cause the monitor to display an image that the observer can view stereoscopically with glasses having, for example, a sheet of red cellophane at the part for the left eye and a sheet of blue cellophane at the part for the right eye using a complementary color method is used.

An example of the stereoscopic display monitor is a monitor that displays a two-parallax image (also referred to as a binocular parallax image) thereby enabling stereoscopic viewing due to binocular parallax (hereinafter, referred to as a two-parallax monitor). Examples of such a two-parallax monitor include an apparatus displaying an image stereoscopically by adopting a shutter system, an apparatus displaying an image stereoscopically by adopting a polarized glass system, and an apparatus displaying an image stereoscopically by adopting a parallax barrier system.

In addition, an example of the stereoscopic display monitor that has been recently put into practical use is a monitor that enables an observer to view a multi-parallax image such as a nine-parallax image stereoscopically with naked eyes, for example, using a light beam controller such as a lenticular lens. This type of stereoscopic display monitor enables stereoscopic viewing due to binocular parallax, and further enables stereoscopic viewing due to motion parallax that provides an image varying according to motion of the viewpoint of the observer.

Figure 2:
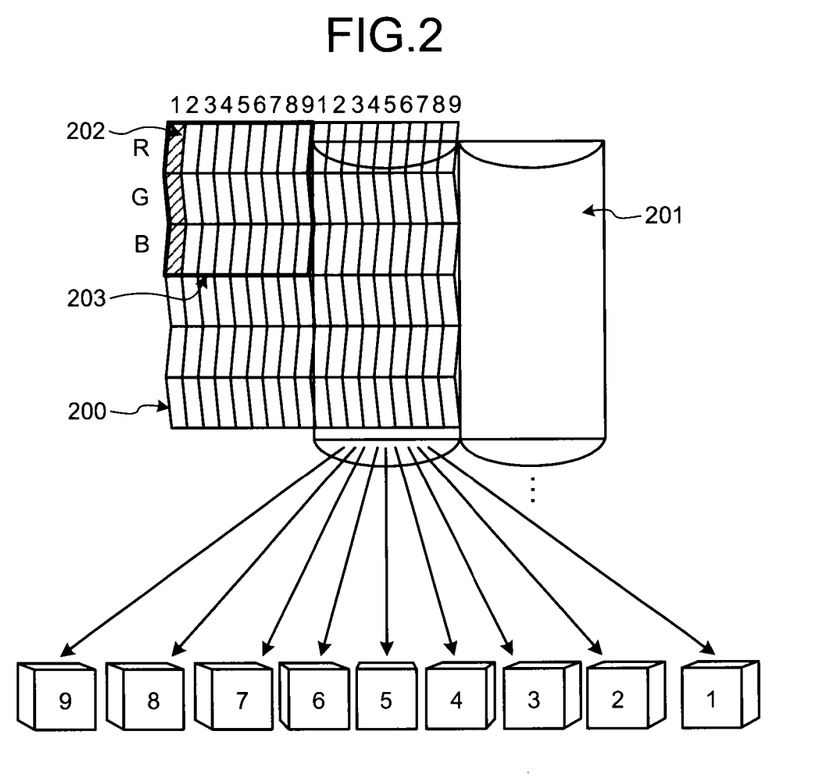
FIG. 2 is a diagram for explaining an example of a stereoscopic display monitor that provides stereoscopic display using a nine-parallax image.

FIG. 2 is a diagram for explaining an example of a stereoscopic display monitor that provides stereoscopic display using a nine-parallax image. The stereoscopic display monitor illustrated in FIG. 2 has a light beam controller on the front surface of a planar display surface 200 such as a liquid panel. For example, in the stereoscopic display monitor illustrated in FIG. 2, a vertical lenticular sheet 201 as a light beam controller having an optical opening extending in a vertical direction is attached to the front surface of a display surface 200.

As illustrated in FIG. 2, in the display surface 200, pixels 202 whose aspect ratio is 3:1 and in each of which three subpixels of red (R), green (G), and blue (B) are arranged in the vertical direction are arranged in a matrix. The stereoscopic display monitor illustrated in FIG. 2 allocates each of the nine pixels at the identical position in the nine-parallax images to nine columns of the pixel 202 to output each of the nine pixels. The nine columns of the pixel 202 is a unit pixel group 203 that displays nine images of different viewpoint positions simultaneously.

In the display surface 200, the nine-parallax image that has been output simultaneously as the unit pixel group 203, are emitted as parallel light by a light emitting diode (LED) backlight, for example, and then radiated multidirectionally by the vertical lenticular sheet 201. When light of each pixel of the nine-parallax image is radiated multidirectionally, light entering the right and left eyes of the observer varies depending on positions of the observer (position of the viewpoint). As a result, the observer can view an imaged subject stereoscopically at each of the nine places illustrated in FIG. 2, for example. In addition, the observer can view the imaged subject stereoscopically at the "5" position illustrated in FIG. 2, as being face to face with the imaged subject, for example. Furthermore, the observer can view an imaged subject stereoscopically at each of the positions other than the "5" position illustrated in FIG. 2, for example, while the imaged subject being oriented differently. Hereinafter, the stereoscopic display monitor explained with reference to FIG. 2 will be described as a nine-parallax monitor.

The first embodiment can be applied to a case where the monitor is a two-parallax monitor and a case where the monitor is a nine-parallax monitor. A case where the monitor 2 is a nine-parallax monitor will be described below.

As illustrated in FIG. 1 again, the external device 4 is an apparatus coupled to the apparatus main body 10 through the interface unit 19 described later. The external device 4 is, for example, a computer-readable storage device, such as a hard disk, a flexible disk, a compact disk read-only memory (CD-ROM), a magneto-optical disk (MO), and a digital versatile disk (DVD). Alternatively, the external device 4 is a printer or the general-purpose monitor described above that is coupled to a terminal device such as a personal computer (PC), a tablet PC, a personal digital assistant (PDA) and a mobile phone operated by a doctor or a laboratory technician working in a hospital.

The apparatus main body 10 creates ultrasonic image data according to reflected waves received by the ultrasonic probe 1. Specifically, the apparatus main body 10 according to the first embodiment is an apparatus that can create three-dimensional ultrasonic image data (hereinafter, referred to as volume data) according to three-dimensional reflected waves received by the ultrasonic probe 1.

As illustrated in FIG. 1, the apparatus main body 10 includes the transmitter-receiver 11, a B-mode processing unit 12, a Doppler processing unit 13, a two-dimensional data processing unit 14, an image memory 15, an internal storage unit 16, a volume data processing unit 17, a control unit 18, and an interface unit 19.

The transmitter-receiver 11 has a trigger generating circuit, a delay circuit, a pulser circuit, and the like and supplies driving signals to the ultrasonic probe 1. The pulser circuit repeatedly generates a rated pulse at a predetermined rate frequency to form transmission ultrasonic waves. The delay circuit applies a delay time that is required to converge the ultrasound wave generated by the ultrasound probe 1 into the form of a beam and to determine transmission directionality and that corresponds to each of the piezoelectric transducer elements, to each of the rate pulses generated by the pulser circuit. The trigger generating circuit applies the driving signal (driving pulse) to the ultrasonic probe 1 at a timing based on the rated pulse. That is to say, the delay circuit varies delay time to provide to each rated pulse, thereby arbitrarily adjusting a transmitting direction from a surface of the piezoelectric transducer elements.

The transmitter-receiver 11 has a function of changing instantly a transmitting frequency, a transmission driving voltage, and the like according to instructions of the control unit 18 described later, in order to execute a predetermined scan sequence. Changing a transmission driving voltage can be achieved by a linear-amplifier-type outgoing circuit that can switch values instantly, or a mechanism electrically switching a plurality of power units.

The transmitter-receiver 11 has an amplifier circuit, an analog-digital (A/D) converter, an adder, and the like and performs various kinds of processing on reflected wave signals received by the ultrasonic probe 1, thereby generating reflected wave data. The amplifier circuit performs gain correction processing by amplifying the reflected wave signals for each channel. The A/D converter converts the reflected wave signals that have been gain-corrected from analog to digital and provides delay time necessary for determining receiving directivity to digital data. The adder performs adding processing of the reflected wave signals that have been processed by the A/D converter and generates the reflected wave data. Adding processing of the adder emphasizes a reflecting component from a direction corresponding to receiving directivity of the reflected wave signals.

As described above, the transmitter-receiver 11 controls transmitting and receiving directivity in transmitting and receiving ultrasonic waves.

The transmitter-receiver 11 according to the first embodiment causes the ultrasonic probe 1 to transmit a three-dimensional ultrasonic beam to the subject P, and creates a three-dimensional reflected wave data from a three-dimensional reflected wave signals received by the ultrasonic probe 1.

The B-mode processing unit 12 receives the reflected wave data from the transmitter-receiver 11 to perform logarithm amplification and envelope detection processing, for example, thereby creating data whose signal strength is represented by a degree of brightness (B-mode data).

The Doppler processing unit 13 performs frequency analysis of speed information from the reflected wave data received by the transmitter-receiver 11 to extract echo components of a moving object such as bloodstream, a tissue, and a contrast agent due to the Doppler effect, thereby creating data (the Doppler data) extracted an average velocity, a dispersion value, a power value, and the like with respect to multiple points.

The B-mode processing unit 12 and the Doppler processing unit 13 according to the first embodiment can process both two-dimensional reflected wave data and three-dimensional reflected wave. That is to say, the B-mode processing unit 12 creates two-dimensional B-mode data from the two-dimensional reflected wave data, and three-dimensional B-mode data from the three-dimensional reflected wave data. The Doppler processing unit 13 creates two-dimensional Doppler data from the two-dimensional reflected wave data, and three-dimensional Doppler data from the three-dimensional reflected wave data.

The two-dimensional data processing unit 14 creates "ultrasonic image data to be displayed" from the two-dimensional data created by the B-mode processing unit 12 or the Doppler processing unit 13. That is to say, the two-dimensional data processing unit 14 creates two-dimensional B-mode image data in which reflected wave strength is represented by a degree of brightness from the two-dimensional B-mode data created by the B-mode processing unit 12. The two-dimensional data processing unit 14 creates two-dimensional color Doppler image data as an average speed image, a dispersion image, a power image, or a combination image thereof representing information of the moving object from the two-dimensional Doppler data created by the Doppler processing unit 13.

The two-dimensional data processing unit 14 converts (by performing a scan convert process) signal columns of scanning lines in ultrasonic scanning to signal columns of scanning lines in video format that is typical in television, thereby creating "ultrasonic image data to be displayed" from the two-dimensional B-mode data or the two-dimensional color Doppler data to output ultrasonic image data to be displayed to the monitor 2. Specifically, the two-dimensional data processing unit 14 performs coordinate transformation depending on scan mode of ultrasonic waves by the ultrasonic probe 1, thereby creating "the ultrasonic image data to be displayed".

The two-dimensional data processing unit 14 creates a composite image in which character information, a scale, a body mark, or the like for various kinds of parameters are composed to the ultrasonic image data to be displayed, to output the composite image to the monitor 2 as a video signal. Hereinafter, an image composed of "character information, a scale, a body mark, or the like for various kinds of parameters" composed for the ultrasonic image data to be displayed is referred to "information image".

The image memory 15 is a memory that stores therein the image data created by the two-dimensional data processing unit 14. The image memory 15 can also store therein the data created by the B-mode processing unit 12 or the Doppler processing unit 13.

The internal storage unit 16 stores therein a control program to perform transmitting and receiving ultrasonic waves, image processing, display processing, and various kinds of data such as diagnostic information (e.g. a patient ID, doctor's findings), diagnostic protocols, and various body marks. The internal storage unit 16 is used for storing the image data in the image memory 15, as necessary.

The volume data processing unit 17 creates the ultrasonic image data to be displayed from the three-dimensional data created by the B-mode processing unit 12 or the Doppler processing unit 13. As illustrated in FIG. 1, the volume data processing unit 17 includes a volume data creation unit 17a, a rendering processing unit 17b, and a composing unit 17c.

The volume data creation unit 17a creates the three-dimensional B-mode image data in which reflected wave strength is represented by a degree of brightness from the three-dimensional B-mode data created by the B-mode processing unit 12. And, the volume data creation unit 17a creates the three-dimensional color Doppler image data as an average speed image, a dispersion image, a power image, or a combination image thereof representing information of the moving object from the three-dimensional Doppler data created by the Doppler processing unit 13. In addition, the volume data creation unit 17a performs coordinate transformation depending on scan mode of ultrasonic waves by the ultrasonic probe 1, thereby creating "volume data" that is the three-dimensional ultrasonic image data.

The rendering processing unit 17b is a unit that performs rendering processing on the volume data in order to create various kinds of images (two-dimensional images) to display the volume data on the monitor 2. An example of rendering processing performed by the rendering processing unit 17b is processing for obtaining a multi planer reconstruction (MPR) image from the volume data using an MPR method. Another example of rendering processing performed by the rendering processing unit 17b is processing by which "Curved MPR" is performed on the volume data or processing by which "Intensity Projection" is performed on the volume data.

An further example of rendering processing performed by the rendering processing unit 17b is volume rendering processing that creates the two-dimensional image reflecting three-dimensional information.

By using these rendering functions, the rendering processing unit 17b performs rendering processing on the volume data that is the three-dimensional ultrasonic image data from a plurality of viewpoints, thereby creating a parallax image group that is composed of predefined number of the parallax images. Specifically, the rendering processing unit 17b performs volume rendering processing on the volume data, thereby creating the parallax image group. More specifically, the rendering processing unit 17b performs volume rendering processing from nine viewpoints because the monitor 2 is a nine-parallax monitor, thereby creating a nine-parallax image composed of nine parallax images.

Figure 3:
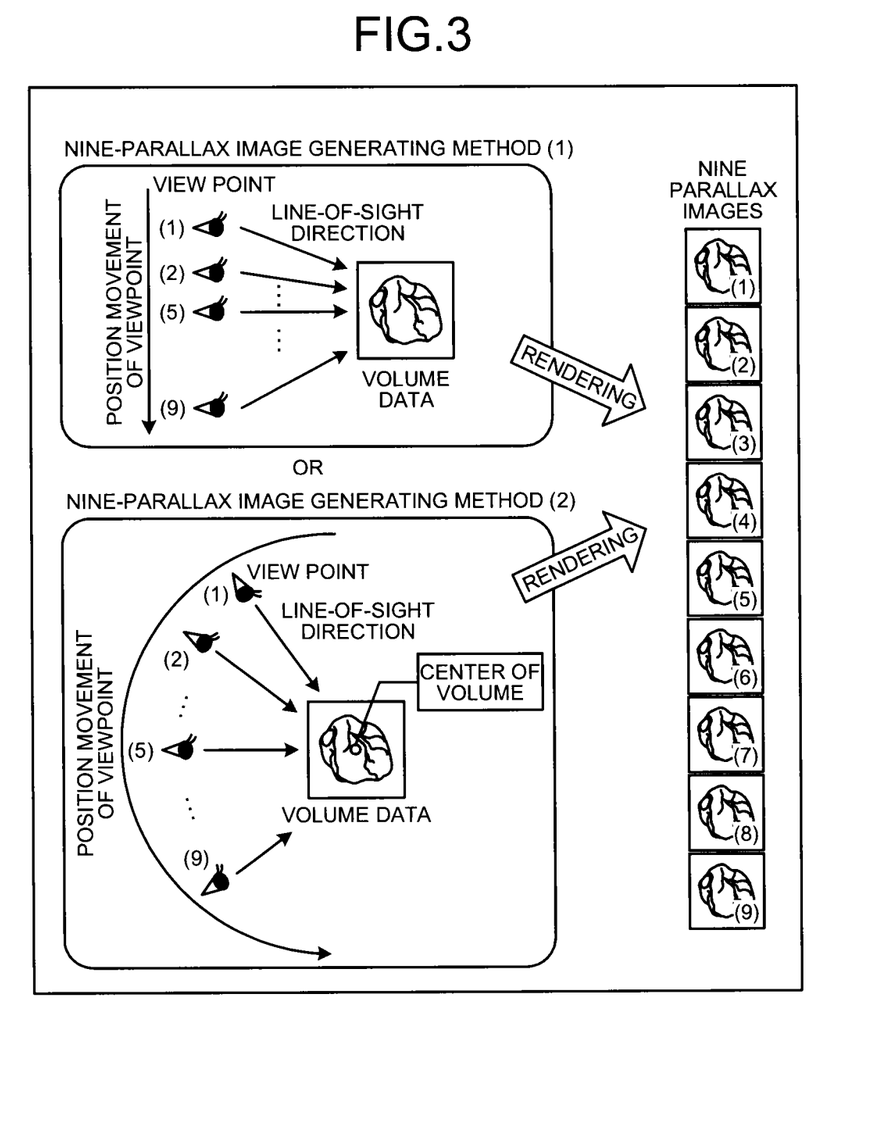
FIG. 3 is a diagram for explaining an example of volume rendering processing according to the first embodiment.

For example, the rendering processing unit 17b performs volume rendering processing illustrated in FIG. 3 under control of the control unit 18 described later, thereby creating nine-parallax image. FIG. 3 is a diagram for explaining example of the volume rendering processing according to the first embodiment.

For example, as illustrated in "nine-parallax image creation method (1)" in FIG. 3, the rendering processing unit 17b receives a parallel projection method as a rendering condition, and further receives a reference viewpoint position (5) and a "one degree" parallax angle. In this case, the rendering processing unit 17b moves the position of the viewpoint in parallel (1) to (9) so that each of the parallax angles is set in increments of "one degree", thereby creating nine parallax images having different parallax angles (angles between line-of-sight directions) by one degree using the parallel projection method. When the parallel projection method is used, the rendering processing unit 17b sets a light source emitting light beams in parallel from infinity along the line-of-sight directions.

Otherwise, as illustrated in "nine-parallax image creation method (2)" in FIG. 3, the rendering processing unit 17b receives a perspective projection method as a rendering condition, and further receives a reference viewpoint position (5) and a "one degree" parallax angle. In this case, the rendering processing unit 17b moves the position of the viewpoint rotationally from (1) to (9) so that each of the parallax angles is set in increments of "one degree" around the center (gravity) of the volume data, the viewpoint, thereby creating nine parallax images having different parallax angles by one degree using the perspective projection method. When the perspective projection method is used, the rendering processing unit 17b sets a point light source or a planar light source emitting light beams radially in three dimensions with the line-of-sight direction centered on each of the viewpoints. When the perspective projection method is used, the viewpoints (1) to (9) may be moved in parallel depending on some rendering conditions.

The rendering processing unit 17b may set a light source that emits light beams multidirectionally in two dimensions with the line-of-sight direction centered with respect to a vertical direction of the volume rendering image displayed, and emits light beams in parallel from infinity along the line-of-sight directions with respect to a horizontal direction of the volume rendering image displayed, thereby performing volume rendering processing by which the parallel projection method and the perspective projection method are used in combination.

The nine parallax images thus created is a parallax image group. In other words, the parallax image group is an ultrasonic image group for stereoscopic display created from the volume data. In the first embodiment, the nine parallax images are converted to an intermediate image arranged in a predetermined format (e.g. in a reticular pattern) by the control unit 18 described later, and are output to the monitor 2 that is a stereoscopic display monitor.

Under control of the control unit 18, the monitor 2 displays the parallax image group created by the rendering processing unit 17b, thereby displaying the stereoscopic image to be recognized by the observer (the operator of the ultrasound diagnosis apparatus) stereoscopically.

Similar to the two-dimensional data processing unit 14, the volume data processing unit 17 creates a composite image group in which information other than the parallax image group (character information, a scale, a body mark, etc.) are composed to the parallax image group to be displayed, to output parallax image group to the monitor 2 as a video signal.

The composing unit 17c illustrated in FIG. 1 is a processing unit provided in the volume data processing unit 17 in order to create the composite image group. Processing of the composing unit 17c will be described in detail later.

Various kinds of image data created by processing of the volume data processing unit 17 are stored in the image memory 15 or the internal storage unit 16.

The control unit 18 controls whole processing of the ultrasound diagnosis apparatus. Specifically, the control unit 18 controls processing of the transmitter-receiver 11, the B-mode processing unit 12, the Doppler processing unit 13, the two-dimensional data processing unit 14, and the volume data processing unit 17 according to various kinds of setting demands input from the operator through the input device 3 or various kinds of control programs and various kinds of data read from the internal storage unit 16. The control unit 18 performs control so that the ultrasonic image data to be displayed stored in the image memory 15 or the internal storage unit 16 is displayed on the monitor 2. The control unit 18 also performs control so that the ultrasonic image data is displayed so as to be output to the external device 4 through the interface unit 19 and the network 100.

The interface unit 19 is an interface for the input device 3, the network 100, and the external device 4. Various kinds of setting information and various kinds of instructions received by the input device 3 from the operator are transferred by the interface unit 19 to the control unit 18. The image data output under control of the control unit 18 is output to the external device 4 through the interface unit 19 and the network 100.

We described the entire structure of the ultrasound diagnosis apparatus according to the first embodiment as above. With this structure, the ultrasound diagnosis apparatus according to the first embodiment creates the volume data that is the three-dimensional ultrasonic image data, thereby creating the parallax image group from the ultrasonic image data thus created. After that, the ultrasound diagnosis apparatus according to the first embodiment displays the parallax image group on the monitor 2, thereby displaying the stereoscopic image that can be recognized stereoscopically by the observer.

Figure 4:
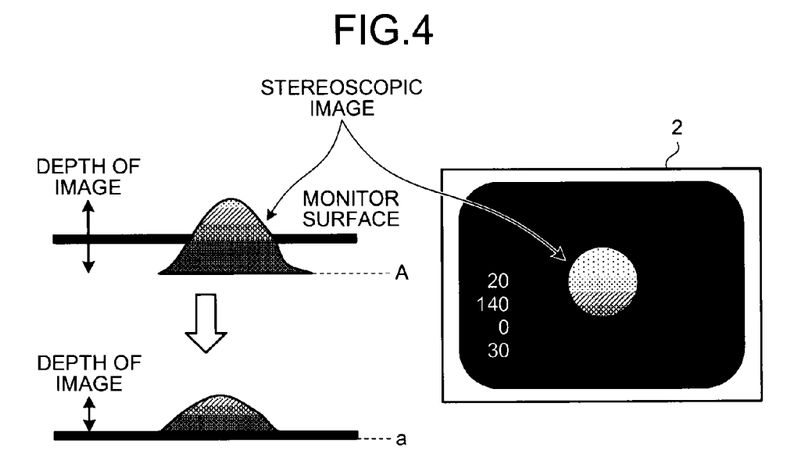
FIG. 4 is a diagram for explaining a problem in the related art.

The image group actually displayed on the monitor 2 is a composite image group of each of the parallax images included in the parallax image group and the information image. However, because the observer refers to the monitor 2 that is a stereoscopic display monitor, the feeling of the depth of the stereoscopic image recognized by the observer is reduced due to factors as described below. FIG. 4 is a diagram for explaining a problem in the related art. The problem described below occurs not only in the stereoscopic image recognized due to the parallax image group based on the volume data created by the ultrasound diagnosis apparatus, but also in the stereoscopic image recognized by the parallax image group based on the volume data created by the medical image diagnosis apparatus such as the X-ray CT apparatus, the MRI apparatus, and the like.

Because medical images require an image quality with contrast, "black" is generally used for a background color on the medical images. In addition, for a background color of the information image displayed along with the medical image, black is generally used. That is to say, the background color for the parallax image group and the background color for the information image are both black. As a result, as illustrated in the right diagram in FIG. 4, the observer recognizes characters or other information along with the stereoscopic image within the background color in black color in the surface of the monitor 2 (hereinafter, referred to as a monitor surface).

As illustrated in the upper left diagram in FIG. 4, the parallax image group is an image group created so as to be recognized by the observer as a stereoscopic image having a depth from, a protruding position from the monitor surface toward the observer side, to a position in the rear side of the monitor surface (refer to a position A in the diagram).

However, human beings generally recognize a position in black color as the deepest position. Therefore, the stereoscopic image actually recognized by the observer is such a stereoscopic image, as illustrated in the lower left diagram in FIG. 4, that has only a depth from, a protruding position from the monitor surface toward the observer side, to a position of the monitor surface (refer to a position a in the diagram). That is to say, the observer recognizes the position A as the position a in the stereoscopic image, whereby the depth of the stereoscopic image is reduced as illustrated in FIG. 4.

The control unit 18 of the ultrasound diagnosis apparatus according to the first embodiment prevents reduction of the feeling of the depth of the medical image viewed stereoscopically, by performing controls described below. That is to say, the control unit 18 performs control so that the "composite image group of the parallax image group and the information image" is displayed on the monitor 2 in such a manner that a first region displaying the parallax image group on the monitor 2 can be distinguished from a second region displaying the information image indicating information other than the parallax image group on the monitor 2. Specifically, the control unit 18 performs control so that the composite image group having different background colors for the first region and the second region is displayed on the monitor 2.

More specifically, the control unit 18 controls the composing unit 17c to create the composite image group having different background colors for the first region and the second region as the composite image group of the parallax image group and the information image in which the first region can be distinguished from the second region.

Figure 5A:
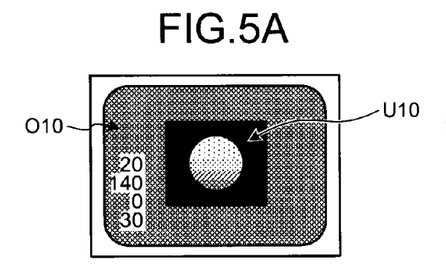
FIG. 5A and FIG. 5B are diagrams for explaining an example of a composite image group according to the first embodiment.
Figure 5B:
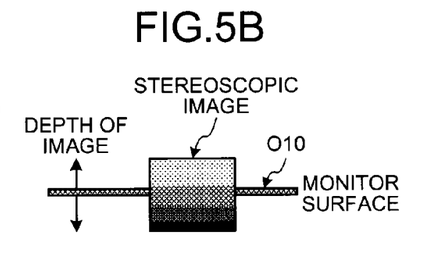
Figure 6A:
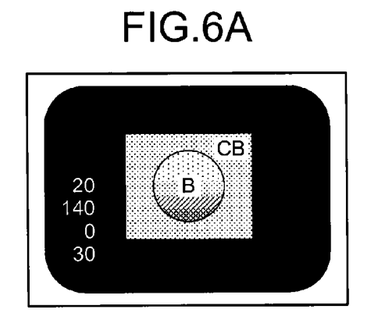
FIG. 6A and FIG. 6B are diagrams for explaining another example of the composite image group according to the first embodiment.
Figure 6B:
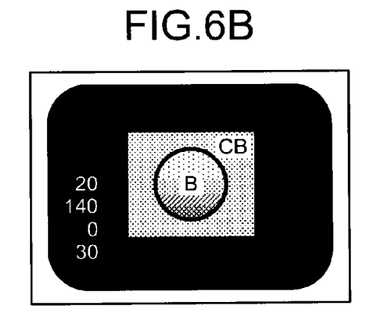

Hereinafter, examples of the composite image group created by the composing unit 17c according to the first embodiment under control of the control unit 18 will be described. FIGS. 5A and 5B are diagrams for explaining an example of the composite image group according to the first embodiment. FIGS. 6A and 6B are diagrams for explaining another example of the composite image group according to the first embodiment.

For example, the control unit 18 performs control so that the composite image group having a background color in black for the first region and a background color in gray for the second region is displayed on the monitor 2. With this control, the composing unit 17c, as illustrated in FIG. 5A, creates a composite image of the parallax image U10 having a background color in black and the information image O10 having a background color in gray. The parallax image U10 illustrated in. FIG. 5A is one parallax image out of the nine parallax images having parallax angles of "one degree" between the respective images, for example. Actually, the composing unit 17c creates nine composite images of the respective nine parallax images having the background color in black and the information image O10 having the background color in gray.

The composing unit 17c makes the respective background color of the nine parallax images displayed on the first region black. When the respective background color of the nine parallax images created by the rendering processing unit 17b are black, the composing unit 17c uses the nine parallax images created by the rendering processing unit 17b as they are in processing described later. When the respective background colors of the nine parallax images created by the rendering processing unit 17b are not black, the composing unit 17c changes the respective background colors of the nine parallax images created by the rendering processing unit 17b to black for use in processing described later.

The composing unit 17c creates the information image in which character and other information is arranged and a background color excluding such information is gray in the second region placed so as to surround the first region. The composing unit 17c composes the respective nine parallax images having the background color in black and the information image having the background color in gray, thereby creating the composite image group of the nine composite images.

The control unit 18 converts the composite image group to the intermediate image described above and displays the intermediate image on the monitor 2. As illustrated in FIG. 5B, the observer of the monitor 2 recognizes character information and the like drawn in the information image O10 having the background color in gray. As illustrated in FIG. 5B, the observer of the monitor 2 recognizes a stereoscopic image having the background color in black and displayed due to the parallax image group. Because the observer recognizes such that a position in gray is nearer to itself than a position in black, the depth of the stereoscopic image having the background color in black is maintained.

The composite image group created by the composing unit 17c is not limited to the composite image group illustrated in FIGS. 5A and 5B. For example, as illustrated in FIG. 6A, the composing unit 17c may changes the background color of the parallax image group to a complementary color "CB" of a color of the parallax image group "B" while retaining the background color in black of the information image under control of the control unit 18. By changing the background color of the parallax image group to the complementary color of the color of the parallax image group, the observer can distinguish the stereoscopic image from the information image.

In addition, as illustrated in FIG. 6B, under control of the control unit 18, the composing unit 17c may change the background color of the parallax image group to a complementary color "CB" of a color of the parallax image group "B" while changing an outline of the composite image group to black for the purpose of emphasis. By changing the background color of the parallax image group to the complementary color of the color of the parallax image group and changing the outline of the parallax image group to black, the observer can recognize that the outline of the stereoscopic image in the first region are placed further than the position of the monitor surface, thereby being able to distinguish the stereoscopic image from the information image.

Furthermore, the example of the composite image group illustrated in FIGS. 6A and 6B may be created so that the background color of the second region where the information image is displayed is an intermediate color of "B" and "CB". Displaying the composite image group also enables the observer to distinguish the stereoscopic image from the information image.

Figure 7:
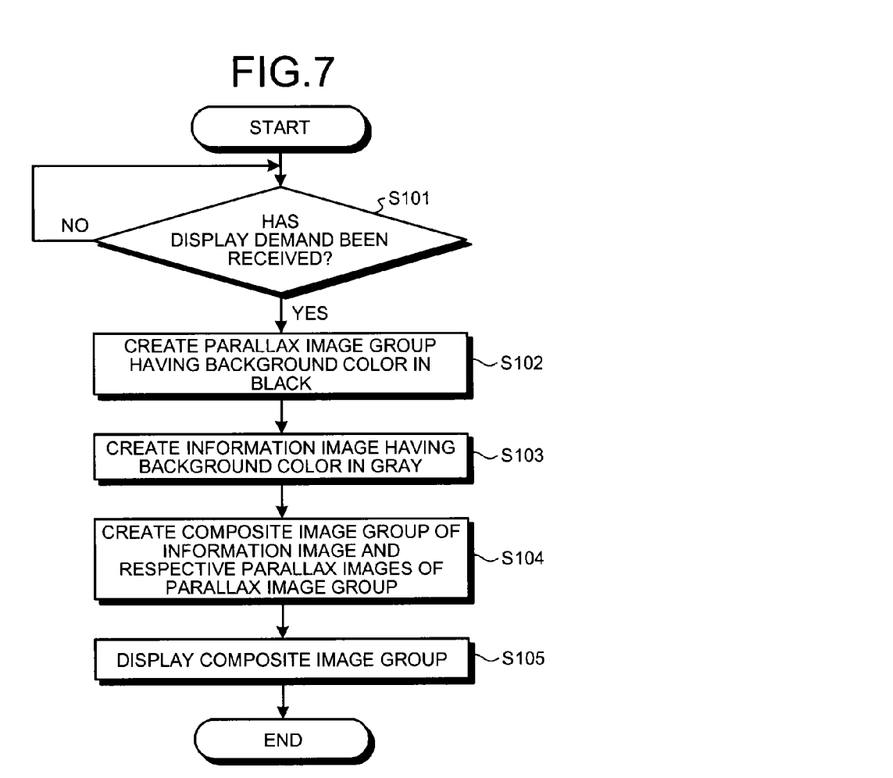
FIG. 7 is a flowchart for explaining processing of the ultrasound diagnosis apparatus according to the first embodiment.

Processing of the ultrasound diagnosis apparatus according to the first embodiment will now be described with reference to FIG. 7. FIG. 7 is a flowchart for explaining processing of the ultrasound diagnosis apparatus according to the first embodiment. With reference to FIG. 7, processing after the volume data is created and the creation conditions of the parallax image group about the volume data such as the viewpoint position, the number of parallax and the parallax angle are set will be described.

As illustrated in FIG. 7, the ultrasound diagnosis apparatus according to the first embodiment determines whether a display demand for the stereoscopic image has been received from the operator through the input device 3 (Step S101). If the display demand has not been received (No at Step S101), the ultrasound diagnosis apparatus according to the first embodiment waits until the display demand is received.

On the other hand, if the display demand has been received (Yes at Step S101), under control of the control unit 18, the rendering processing unit 17b creates the parallax image group having the background color in black (Step S102), while the composing unit 17c creates the information image having the background color in gray (Step S103).

After that, the composing unit 17c creates a composite image group of the information image and the respective parallax images of the parallax image group whose size is matched to that of the first region (Step S104). Specifically, the composing unit 17c creates an information image having the background color in gray whose shape is matched to that of the second region. Then, under control of the control unit 18, the monitor 2 displays the composite image group (Step S105), to complete processing.

As described above, in the first embodiment, the control unit 18 displays "the composite image group of the parallax image group and the information image" in which the first region displaying the parallax image group on the monitor 2 can be distinguished from the second region displaying the information image indicating information other than the parallax image group. That is to say, in the first embodiment, the control unit 18 performs control so that the composing unit 17c creates the composite image group of the information image and the parallax image group in which the first region can be distinguished from the second region, having different background colors for the first region and the second region, and displays the composite image group on the monitor 2.

Specifically, the control unit 18 performs control so that the composing unit 17c creates the composite image group of the parallax image group having the background color in black for the first region and the information image having the background color in gray for the second region where the first region can be distinguished from the second region, and displays the composite image group on the monitor 2.

With this control described above, the observer can feel that the information image displayed in the second region is placed on the monitor surface, while the background of the stereoscopic image displayed in the first region is placed further than the monitor surface. As a result, in the first embodiment, reduction of the feeling of the depth of the medical image viewed stereoscopically can be prevented. The processing of the composing unit 17c according to the first embodiment may be performed by the two-dimensional data processing unit 14.

In the second embodiment, a case where a composite image group is created with a different method from the first embodiment will be described.

Although an ultrasound diagnosis apparatus according to the second embodiment is structured similar to the ultrasound diagnosis apparatus according to the first embodiment described with reference to FIG. 1, control processing of the control unit 18 to the composing unit 17c differs from that in the first embodiment. Hereinafter, the difference will be mainly described.

Figure 8A:
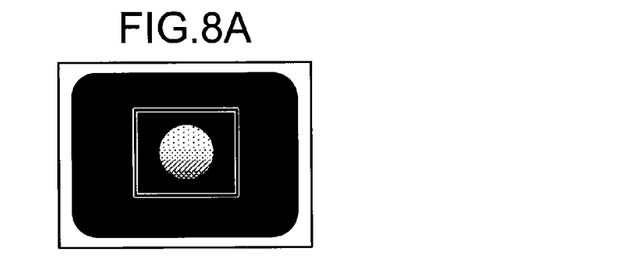
FIG. 8A and FIG. 8B are diagrams for explaining a composite image group according to a second embodiment.
Figure 8B:
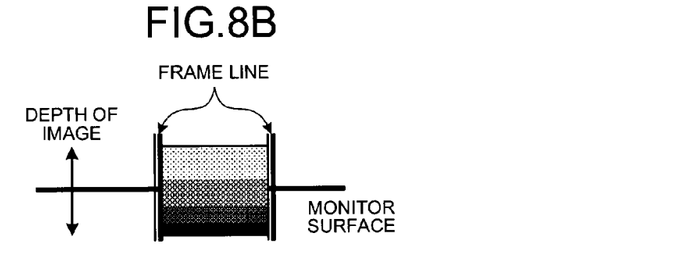

The control unit 18 according to the second embodiment performs control so that a composite image group in which a frame line surrounding the border of the first region and the second region is drawn, is displayed on the monitor 2. FIGS. 8A and 8B are diagrams for explaining a composite image group according to the second embodiment.

For example, as illustrated in FIG. 8A, the composing unit 17c creates a composite image group in which a border of the first region and the second region is surrounded with a white double line under control of the control unit 18.

When the respective background colors of the nine parallax images created by the rendering processing unit 17b are black, the composing unit 17c uses the nine parallax images created by the rendering processing unit 17b as they are in processing described later. In the second region, the composing unit 17c creates an information image in which character information and the like is arranged and the background color excluding the character information and the like is black, similar to the related art. The composing unit 17c then composes the respective nine parallax images and the information image. Subsequently, the composing unit 17c draws a white double line surrounding respective outlines of the nine parallax images, thereby creating the composite image group of the nine composite images.

The control unit 18 converts the composite image group to an intermediate image to be displayed to the monitor 2. As a result, as illustrated in FIG. 8B, the observer of the monitor 2 recognizes character information and the like drawn in the information image bounded with a frame line. As illustrated in FIG. 8B, the observer of the monitor 2 recognizes the stereoscopic image having the background color in black and bounded with the frame line. Because the observer can distinguish the information image from the stereoscopic image due to the frame line, the depth of the stereoscopic image is maintained.

Such a discrimination effect by the frame line is referred to as a sticking effect or a frame effect. However, when a subject viewed stereoscopically is bounded with an image frame (frame line), a difference may occur between an image to the right eye and an image to the left eye of the observer, resulting in sight conflict making viewing unstable, or the subject is viewed as sticking to the frame line resulting in reduction of stereoscopic effect, thus the subject is viewed as deformed.

To solve the problem above, the control unit 18 may set the image frame (frame line) so as to be viewed in a different position from the monitor display surface, enlarge the size of a screen that weakens existence of the frame and make the position of the display surface indeterminate, or perform control based on an aerial image system or a spatial image system. An aerial image is an image in which a display image is formed in the air. When observing an aerial image existence position on a display surface becomes indeterminate, and an effect is obtained that a reproduction space is hardly fixed on the display surface. A spatial image is an image formed with multilayer display surface, or due to image surface movement, or the like. When observing a spatial image, similar effect to that in observing an aerial image can be achieved.

Figure 9:
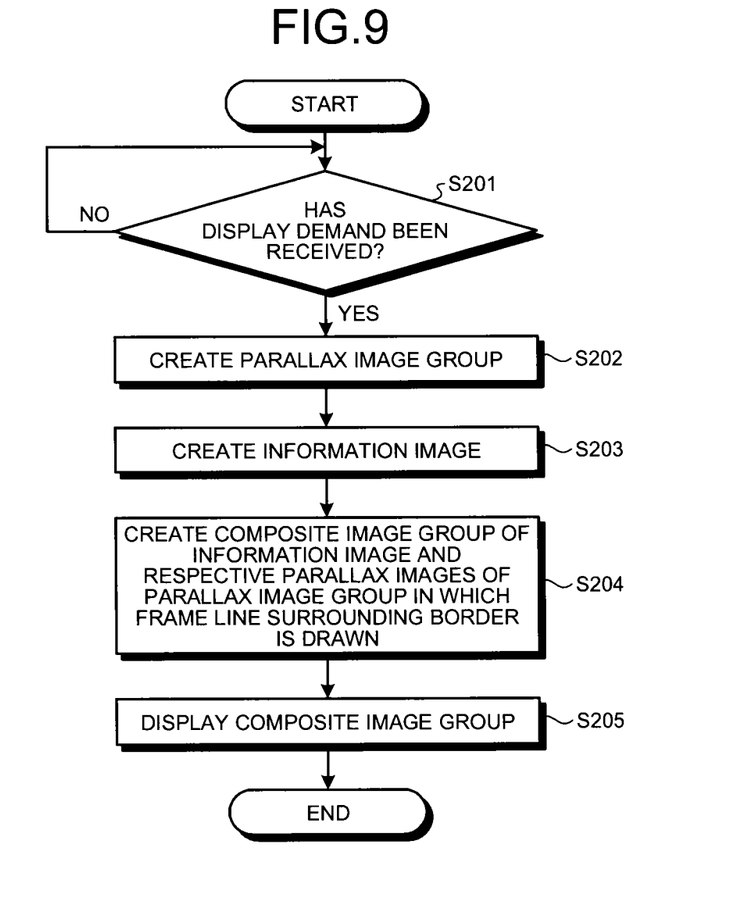
FIG. 9 is a flowchart for explaining processing of an ultrasound diagnosis apparatus according to the second embodiment.

Processing of the ultrasound diagnosis apparatus according to the second embodiment will now be described with reference to FIG. 9. FIG. 9 is a flowchart for explaining processing of the ultrasound diagnosis apparatus according to the second embodiment. With reference to FIG. 9, processing after the volume data is created and the creation conditions of the parallax image group about the volume data such as the viewpoint position, the number of parallax and the parallax angle are set will be described.

As illustrated in FIG. 9, the ultrasound diagnosis apparatus according to the second embodiment determines whether a display demand for the stereoscopic image has been received from the operator through the input device 3 (Step S201). If the display demand has not been received (No at Step S201), the ultrasound diagnosis apparatus according to the second embodiment waits until the display demand is received.

On the other hand, if the display demand has been received (Yes at Step S201), under control of the control unit 18, the rendering processing unit 17b creates a parallax image group having the background color in black (Step S202), while the composing unit 17c creates an information image having the background color in black (Step S203).

After that, the composing unit 17c creates a composite image group of the information image and the respective parallax images of the parallax image group whose size is matched to that of the first region and in which a frame line is drawn on the boundary (Step S204). Specifically, the composing unit 17c creates the information image having the background color in black whose shape is matched to that of the second region. Then, under control of the control unit 18, the monitor 2 displays the composite image group (Step S205), to complete processing.

As described above, in the second embodiment, the control unit 18 performs control so that the composing unit 17c creates the composite image group in which a frame line surrounding a border of the first region and the second region is drawn, and displays the composite image group on the monitor 2.

With this control described above, the observer can distinguish the first region from the second region due to the line. That is to say, in the second embodiment, recognition of the observer that the stereoscopic image and the information image are in the same depth position can be prevented, even though the stereoscopic image and the information image have the same background color. As a result, also in the second embodiment, reduction of the feeling of the depth of the medical image viewed stereoscopically can be prevented. The processing of the composing unit 17c according to the second embodiment may be performed by the two-dimensional data processing unit 14.

In the third embodiment, processing performed when the parallax image group is output for printing or displayed on a general-purpose monitor will be described.

When observing a stereoscopic image, an observer sometimes desires to output the image observed as two-dimensional data. However, a stereoscopic image is recognized when a plurality of parallax images are displayed. When a plurality of parallax images are replayed on a general-purpose monitor or printed, the image thus output is viewed double or out of focus. That is to say, a plurality of parallax images is unsuitable for image to be output. This means that an image in which a plurality of parallax images are not superimposed is required in order to output the image for printing or to observe the image on a general-purpose monitor.

Therefore, the control unit 18 according to the third embodiment performs control so that image data viewed from the specific viewpoint is extracted from the parallax image group recognized as a stereoscopic image and is output to the external device 4.

The control unit 18 performs the following two output controls. In a first output control, the control unit 18 extracts a parallax image from a viewpoint positioned in the center of all of the viewpoints used for creating the parallax image group, as image data viewed from the specific viewpoint. In a second output control, the control unit 18 extracts a parallax image corresponding to the stereoscopic image observed by the observer referring to the monitor 2, as image data viewed from the specific viewpoint.

If image data corresponding to the image data viewed from the specific viewpoint exists in the parallax image group, the control unit 18 selects the corresponding image data and outputs the image data to the external device 4. On the other hand, if image data corresponding to the image data viewed from the specific viewpoint does not exist in the parallax image group, the control unit 18 causes the rendering processing unit 17b to create image data viewed from the specific viewpoint and outputs the image data to the external device 4.

Figure 10A:
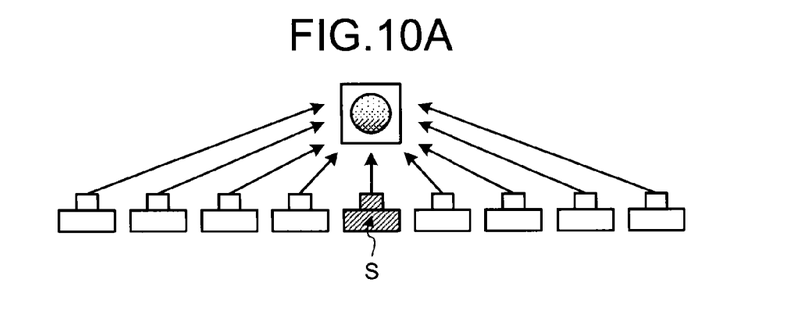
FIG. 10A, FIG. 10B, and FIG. 10C are diagrams for explaining a control unit according to a third embodiment.
Figure 10B:
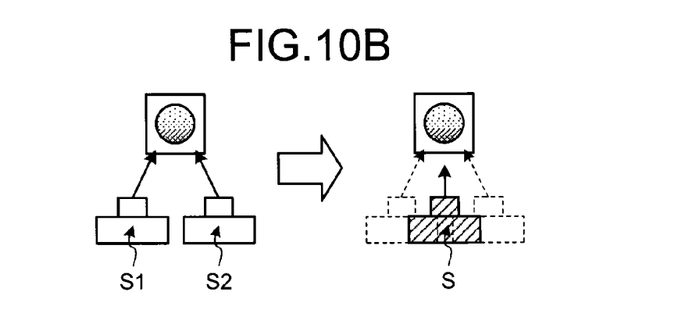
Figure 10C:
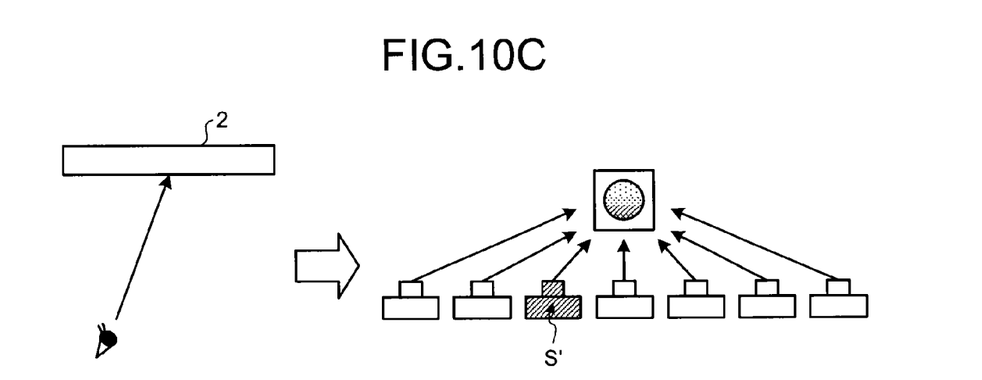

Hereinafter, examples of output controls performed by the control unit 18 according to the third embodiment will be described with reference to FIGS. 10A, 10B, and 10C. FIGS. 10A, 10B, and 10C are diagrams for explaining a control unit according to the third embodiment.

For example, as illustrated in FIG. 10A, when performing a first output control, the control unit 18 extracts a parallax image from a viewpoint S positioned in the center of all of the viewpoints out of the nine-parallax image recognized as a stereoscopic image, thereby outputting data of the parallax images viewed from the viewpoint S to the external device 4.

As illustrated in FIG. 10A, when performing the first output control, if the monitor 2 is a nine-parallax monitor whose number of parallax is odd, extract processing performed by the control unit 18 can be performed by selecting a parallax image from the parallax image group existing. However, if the monitor 2 is a two-parallax monitor, for example, whose number of parallax is even, a parallax image viewed from a viewpoint positioned in the center of all of the viewpoints does not exist.

In such a case, as illustrated in FIG. 10B, the control unit 18 sets a viewpoint S between a viewpoint S1 and the viewpoint S2 adjacent to the center position of all of the viewpoints. As illustrated in FIG. 10B, the control unit 18 then controls the rendering processing unit 17b to create the parallax image viewed from the viewpoint S by performing volume rendering processing on the volume data. After that, the control unit 18 outputs data of the parallax images viewed from the viewpoint S newly created to the external device 4.

As illustrated in FIG. 10O, when performing the second output control, the control unit 18 obtains a line-of-sight direction of the observer referring to the monitor 2 in order to identify a parallax image corresponding to the stereoscopic image observed by the observer referring to the monitor 2. The control unit 18 obtains a line-of-sight direction of the observer to the monitor 2 using a camera having a facial recognition function attached to the monitor 2, for example. The camera performs tracking a face of the observer in an actual space using the facial recognition function, then, determines the line-of-sight direction of the observer to the monitor 2 from a direction of the face recognized. The line-of-sight direction recognized by the camera is transferred to the control unit 18.

After that, the control unit 18 extracts a parallax image corresponding to the line-of-sight direction of the observer from the parallax image group. If a parallax image from a viewpoint S' corresponding to the line-of-sight direction of the observer exists in the parallax image group displayed, the control unit 18 selects data of the corresponding parallax image so as to be output to the external device 4 (refer to FIG. 10O). On the other hand, if a parallax image viewed from the viewpoint S' corresponding to the line-of-sight direction of the observer does not exist in the parallax image group displayed, the control unit 18 sets the viewpoint S' for the volume data. Then, the control unit 18 controls the rendering processing unit 17b to create the parallax image viewed from the viewpoint S' newly created by volume rendering processing using the volume data. The control unit 18 then outputs the data of the parallax image viewed from the viewpoint S' newly created by the rendering processing unit 17b to the external device 4.

The control unit 18 according to the third embodiment may extract the parallax image from the composite image group according to the first embodiment or the second embodiment as the parallax image data to be output. In this case, if a composite image of the specific viewpoint does not exist, the control unit 18 causes the rendering processing unit 17b to newly create the parallax image of the specific viewpoint, and further causes the composing unit 17c to newly create a composite image of the information image and the parallax image of the specific viewpoint.

Figure 11:
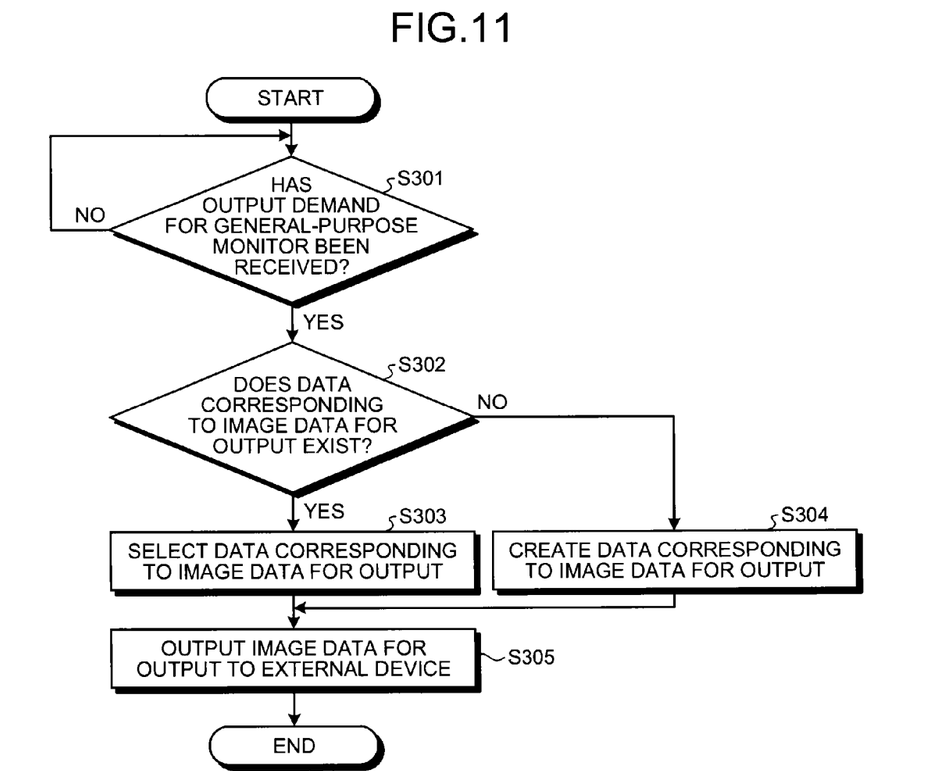
FIG. 11 is a flowchart for explaining processing of an ultrasound diagnosis apparatus according to the third embodiment.

Processing of the ultrasound diagnosis apparatus according to the third embodiment will now be described with reference to FIG. 11. FIG. 11 is a flowchart for explaining processing of the ultrasound diagnosis apparatus according to the third embodiment.

As illustrated in FIG. 11, the ultrasound diagnosis apparatus according to the third embodiment determines whether an output demand for a general-purpose monitor has been received from the operator through the input device 3 (Step S301). If the output demand has not been received (No at Step S301), the ultrasound diagnosis apparatus according to the third embodiment waits until the output demand is received.

On the other hand, if the output demand has been received (Yes at Step S301), the control unit 18 determines whether data corresponding to the image data to be output exists (Step S302). If the data exists (Yes at Step S302), the control unit 18 selects data corresponding to the image data to be output (Step S303). If the composite image group is a subject for extraction and if the data for extraction exists (Yes at Step S302), data selected at Step S303 is data of the composite image.

If the data does not exist (No at Step S302), under control of the control unit 18, the rendering processing unit 17b creates data corresponding to the image data to be output (Step S304). If the composite image group is a subject for extraction and if the data for extraction dose not exist (No at Step S302), the rendering processing unit 17b and the composing unit 17c create new composite image data.

After processing at Step S303 or Step S304, the control unit 18 outputs the image data to be output to the external device 4 (Step S305) to complete processing.

As described above, in the third embodiment, the control unit 18 performs control so that the image data of the specific viewpoint is extracted from the parallax image group recognized as a stereoscopic image and is output to the external device 4. As a result, in the third embodiment, an image viewed from one viewpoint, rather than images in a parallax image group viewed from a plurality of viewpoints can be output.

An example is described above where the image data from the specific viewpoint is one parallax image from one viewpoint or one composite image. However, the image data output to the external device 4 by the processing of the control unit 18 according to the third embodiment may be a plurality of parallax images or a plurality of composite images. That is to say, in the third embodiment, the specific viewpoint may be a plurality of viewpoints, rather than one viewpoint.

For example, the monitor 2 is a nine-parallax monitor while a monitor coupled to the external device 4 is a nine-parallax monitor. In this case, the control unit 18 outputs a nine-parallax image or nine composite images displayed on the monitor 2 as a stereoscopic image, as image data viewed from the specific viewpoint to the external device 4. For another example, the monitor 2 is a nine-parallax monitor while a monitor coupled to the external device 4 is a five-parallax monitor that displays a stereoscopic image by displaying five parallax images. In this case, the control unit 18 outputs five images selected from the nine-parallax image or the nine composite images displayed on the monitor 2 as a stereoscopic image, as image data viewed from the specific viewpoint. Specifically in an example, the control unit 18 outputs the parallax image group viewed from five viewpoints with the viewpoint S centered illustrated in FIG. 10A as image data from the specific viewpoint and outputs the parallax image group to the external device 4. Specifically in another example, the control unit 18 outputs the parallax image group viewed from five viewpoints with the viewpoint S' centered illustrated in FIG. 10B as image data viewed from the specific viewpoint and outputs the parallax image group to the external device 4. Specifically in a further example, the control unit 18 controls the volume data processing unit 17 to newly create a five-parallax image or five composite images displayed as a stereoscopic image on a five-parallax monitor, then outputs the five-parallax image or the five composite images to the external device 4.

Otherwise, for example, the monitor 2 is a nine-parallax monitor while a monitor coupled to the external device 4 is a two-parallax monitor. In this case, the control unit 18 outputs two images selected from the nine-parallax image or the nine composite images displayed on the monitor 2 as a stereoscopic image, as image data viewed from the specific viewpoint. Specifically in an example, the control unit 18 outputs the parallax image viewed from the viewpoint S and the parallax image viewed from a viewpoint positioned on the right side of the viewpoint S illustrated in FIG. 10 to the external device 4 as image data from the specific viewpoint. Specifically in another example, the control unit 18 controls the volume data processing unit 17 to newly create a two-parallax image or two composite images displayed as a stereoscopic image on a two-parallax monitor, then outputs the two-parallax image or the two composite images to the external device 4.

In addition, for example, the monitor 2 is a nine-parallax monitor while a monitor coupled to the external device 4 is a 18-parallax monitor that displays a stereoscopic image by displaying 18 parallax images. In this case, the control unit 18 selects a nine-parallax image or the nine composite images displayed as a stereoscopic image on the monitor 2. Subsequently, the control unit 18 newly sets nine viewpoint positions in addition to the viewpoints used in creating the nine-parallax image or the nine composite images displayed as a stereoscopic image on a the monitor 2. Then, the control unit 18 controls the volume data processing unit 17 to create the nine parallax images or the nine composite images using the nine viewpoints newly created. After that, the control unit 18 outputs the 18 parallax images or the 18 composite images to the external device 4 as image data viewed from the specific viewpoint. The control unit 18 performs processing described above, by obtaining information on a stereoscopic view mode of a monitor coupled to the external device 4, from the external device 4 or the operator of the external device 4.

Furthermore, for example, a monitor coupled to the external device 4 is a nine-parallax monitor and receives information of a referential viewpoint position from the operator of the external device 4. If a nine-parallax image or nine composite images with the referential viewpoint position whose information is received centered are already created, the control unit 18 outputs the image data of the nine-parallax image or the nine composite images to the external device 4 as image data from the specific viewpoint. On the other hand, image data that satisfies a demand from the operator of the external device 4 is not created yet, the control unit 18 controls the volume data processing unit 17 to create the nine-parallax image or nine composite images with the referential viewpoint position whose information is received centered, then outputs the nine-parallax image or nine composite images to the external device 4. The number of the referential viewpoint position whose information is received from the operator of the external device 4 may be more than one. Information received from the operator of the external device 4 may include information on a parallax angle in addition to information on the referential viewpoint position.

As described above, if image data that satisfies the condition received from the operator of the external device 4 is created already in the apparatus main body 10, the control unit 18 outputs the image data as image data from the specific viewpoint. If image data that satisfies the condition received from the operator of the external device 4 is not created yet in the apparatus main body 10, the control unit 18 controls the volume data processing unit 17 to create corresponding image data, and outputs the data to the external device 4.

In the first to third embodiments, an example is described where the monitor 2 is a nine-parallax monitor. However, the first to third embodiments described above can be applied to an example where the monitor is a two-parallax monitor.

In the first to third embodiments, an example is described where an image displayed on the monitor 2 is a volume rendering image. However, the first to third embodiments described above can be applied to an example where the image displayed on the monitor 2 is a multi-planar reformation (MPR) image that is created by MPR from the volume data.

In the first to third embodiments, an example is described where the composite image group for preventing reduction of a feeling of depth is displayed or data of the stereoscopic image to be output is extracted in the ultrasound diagnosis apparatus that is a medical image diagnosis apparatus. However, the processing described above in the first to third embodiments may be performed in a medical image diagnosis apparatus such as an X-ray CT apparatus or an MRI apparatus that can create volume data.

The processing described above in the first to third embodiments may be performed by an image processing apparatus that is installed independent from the medical image diagnosis apparatus. Specifically, an image processing apparatus having functions of the volume data processing unit 17 and the control unit 18 illustrated in FIG. 1 may perform the processing described in the first to third embodiment by receiving volume data that is three-dimensional medical image data from a database of Picture archiving and communication systems (PACS) that controls various kinds of medical image data, a database of an electronic health record system that controls electronic health records having medical images attached thereto, or the like.

As described above, according to the first to the third embodiments, reduction of the feeling of the depth of the medical image viewed stereoscopically can be prevented.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
a rendering processor configured to perform rendering processing from a plurality of viewpoints on volume data that is three-dimensional medical image data to create a parallax image group composed of a predefined number of parallax images;
a display to display the parallax image group created by the rendering processor to display a stereoscopic image recognized stereoscopically by an observer; and
control circuitry configured to perform control so that a composite image group of the parallax image group and an information image is displayed on the display in such a manner that a first region displays the parallax image group on the display with a black background and a second region, which is placed so as to surround the first region, displays the information image indicating information other than the parallax image group on the display with a background of a color which is other than black.

2. The medical image diagnosis apparatus according to claim 1, wherein the control circuitry performs control so that image data viewed from at least one specific viewpoint is extracted from the parallax image group or the composite image group recognized as the stereoscopic image and is output to a given external device.

3. The medical image diagnosis apparatus according to claim 2, wherein the control circuitry extracts image data of a parallax image or a composite image, viewed from a viewpoint positioned in center of all of the viewpoints used for creating the parallax image group, as image data viewed from the specific viewpoint.

4. The medical image diagnosis apparatus according to claim 2, wherein the control circuitry extracts image data of at least one parallax image or image data of at least one composite image, corresponding to the stereoscopic image observed by the observer referring to the display, as image data viewed from the specific viewpoint.

5. The medical image diagnosis apparatus according to claim 2, wherein
if image data corresponding to the image data viewed from the specific viewpoint exists in the parallax image group or the composite image group, the control circuitry is configured to select the corresponding image data and output the image data to the given external device; and
if image data corresponding to the image data viewed from the specific viewpoint does not exist in the parallax image group or the composite image group, the control circuitry is configured to cause the rendering processor to create image data viewed from the specific viewpoint and output the image data to the given external device.

6. The medical image diagnosis apparatus according to claim 1, wherein the control circuitry performs control so that a composite image group having the black background for the first region and a background color in gray for the second region is displayed on the display.

7. The medical image diagnosis apparatus according to claim 1, wherein the control circuitry performs control so that a composite image group in which a frame line surrounding a border of the first region and the second region is drawn is displayed on the display.

8. The medical image diagnosis apparatus according to claim 1, further comprising:
information image creating circuitry configured to create the information image as a flat image.

9. The medical image diagnosis apparatus according to claim 1, wherein the information image is not a non-stereoscopic image.

10. The medical image diagnosis apparatus according to claim 1, wherein the first and second regions are adjacent to each other and are non-overlapping.

11. The medical image diagnosis apparatus according to claim 1, wherein
the information image is a flat image, and
the information image includes parameters associated with ultrasonic image data.

12. The medical image diagnosis apparatus according to claim 1, wherein the information image includes one of a scale and a body mark for parameters associated with ultrasonic image data.

13. An image processing apparatus comprising:
a rendering processor configured to perform rendering processing from a plurality of viewpoints on volume data that is three-dimensional medical image data to create a parallax image group composed of a predefined number of parallax images;
a stereoscopic display to display the parallax image group created by the rendering processor to display a stereoscopic image recognized stereoscopically by an observer; and
control circuitry configured to perform control so that a composite image group of the parallax image group and an information image is displayed on the stereoscopic display in such a manner that a first region displays the parallax image group on the stereoscopic display with a black background and a second region, which is placed so as to surround the first region, displays the information image indicating information other than the parallax image group on the stereoscopic display with a background of a color which is other than black.

14. An ultrasound diagnosis apparatus comprising:
an ultrasonic probe configured to scan a subject in two dimensions using ultrasonic waves, scan the subject in three dimensions, and acquire data of the subject;
a rendering processor configured to perform rendering processing from a plurality of viewpoints on volume data that is three-dimensional medical image data based on the acquired data to create a parallax image group composed of a predefined number of parallax images;
a display to display the parallax image group created by the rendering processor to display a stereoscopic image recognized stereoscopically by an observer; and
control circuitry configured to perform control so that a composite image group of the parallax image group and an information image is displayed on the display in such a manner that a first region displays the parallax image group on the display with a black background and a second region, which is placed so as to surround the first region, displays the information image indicating information other than the parallax image group on the display with a background of a color which is other than black.

* * * * *